United States Patent

Panseri et al.

[11] Patent Number: 5,936,103
[45] Date of Patent: Aug. 10, 1999

[54] PROCESS FOR THE PREPARATION OF AROMATIC COMPOUNDS CONTAINING A HETEROCYCLIC SYSTEM

[75] Inventors: Pietro Panseri, Bergamo; Giambattista Castelli, Presezzo; Vittorio Messori, Milan, all of Italy

[73] Assignee: Borregaard Italia S.p.A., Milan, Italy

[21] Appl. No.: 09/070,913

[22] Filed: May 4, 1998

[30] Foreign Application Priority Data

May 8, 1997 [IT] Italy ................................ M197A1063

[51] Int. Cl.$^6$ ................................................. C07D 317/44
[52] U.S. Cl. ............................................................ 549/437
[58] Field of Search ............................................... 549/437

[56] References Cited

U.S. PATENT DOCUMENTS 3,436,403  4/1969  Cornforth .
3,726,924  4/1973  Leimgruber et al. .

OTHER PUBLICATIONS

Franz Dallacker, et al., Zeitschrift Fur Naturforschung, Teil B: Anorganische Chemie, Organische Chemie, vol. 34b, No. 10, pp. 1434 to 1442, "Darstellung und Eigenschaften von Naphtho [1.2–d]– und Naphtho [2.3–d]–1,3–dioxolen", Oct. 1979.

Robert E. Zelle, et al., Tetrahedron Letters, vol. 32, No. 22, pp. 2461 to 2464, "A Simple, High–Yielding Method for the Methylenation of Catechols", May 27, 1991.

Primary Examiner—Johann Richter
Assistant Examiner—Taofiq A. Solola
Attorney, Agent, or Firm—Oblon, Spivak, McClelland, Maier & Neustadt, P.C.

[57] ABSTRACT

Process for the preparation of aromatic compounds containing a heterocyclic system, having general formula (II):

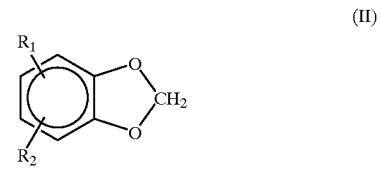

(II)

which comprises reacting catechol, optionally substituted, with a methylene dihalide in a basic environment and in the presence of a solvent medium consisting of N-methylpyrrolidone.

8 Claims, No Drawings

PROCESS FOR THE PREPARATION OF AROMATIC COMPOUNDS CONTAINING A HETEROCYCLIC SYSTEM

The present invention relates to a process for the preparation of aromatic compounds containing a heterocyclic system.

More specifically, the present invention relates to a process for the preparation of 1,3-benzodioxols optionally substituted in the benzene ring, for example with alkyl or aldehyde groups.

1,3-benzodioxols, such as for example, 1,3-methylenedioxybenzene (MDB), are products known as intermediates suitable for the preparation of products which can be used in agriculture and the pharmaceutical and cosmetic industry.

Processes for the production of 1,3-benzodioxols consist in reacting catechol and a methylene dihalide in the presence of a base and a catalyst according to the reaction scheme (I):

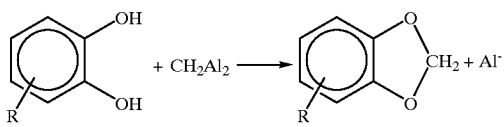

Methods for the preparation of 1,3-benzodioxols are known in scientific literature, French patent 1,502,914, for example, describes a process for the preparation of aromatic compounds containing a heterocyclic system which comprises the reaction of catechol with a methylene dihalide according to reaction scheme (I).

The reaction takes place at a high temperature, at about 120°–130° C., and in the presence of a highly polar, aprotic solvent such as, for example, dimethylsulfoxide (DMSO). At the end, the reaction product is recovered by the conventional extraction/distillation techniques.

U.S. Pat. No. 4,082,774 discloses the preparation of MDB starting from catechol and methylene dihalide.

In particular, according to the process of the U.S. patent, MDB is basically prepared in two steps. In the first step, a solution of the di-anion of catechol is prepared by the reaction of the latter with a salt or alkaline hydroxide in a solvent consisting of DMSO and water. In the second step the di-anion solution is added to a solution of methylene dihalide in DMSO.

The MDB product is recovered from the reaction mixture by distillation with water vapour and extraction with ether.

The above processes have the common characteristic of using DMSO as solvent. The use of DMSO as reaction solvent in the synthesis of 1,3-benzodioxols allows, with respect to other polar aprotic solvents such as dimethylformamide, dimethylacetamide or silfolane, complete conversion of the catechol and high selectivity to the useful product, to be obtained.

The use of DMSO, however, is not without drawbacks. As also acknowledged in "Industrial Chemistry & Engineering Symposium Series", Nr. 134, 1994, pages 563–574, DMSO is unstable at high temperatures and in addition, in the presence of alkaline metal halides, present in the reaction mixture of MDB, the decomposition temperature drops by about 50° C., not allowing a synthesis temperature which is sufficiently distant from the decomposition temperature. Under these conditions, the decomposition of the DMSO can develop an explosive trend which is typical of "Run Away" reactions.

In addition, again as a result of instability, the recovery of the DMSO from the reaction mixture is extremely difficult as it must be carried out under a considerably forced vacuum to lower the distillation temperature. In spite of this, a certain decomposition of the solvent cannot be avoided, with the formation of extremely badly-smelling and toxic mercaptane by-products which are difficult to dispose of.

Finally, DMSO forms azeotropic mixtures with benzodioxols, for example with the product 1,3-methylenedioxybenzene, which make it difficult to recover both the useful product and the solvent.

Alternative methods for the preparation of benzodioxols have been proposed in literature, which are not subject to the use of the solvent DMSO.

U.S. Pat. No. 4,183,861 describes a method for the preparation of benzodioxols which consists in reacting catechol, optionally substituted, with methylene chloride without a solvent and in the presence of a catalyst selected from ammonium or phosphonium salts.

There are no safety problems with the use of catalysts based on quaternary salts but it is necessary to operate under pressure and high selectivities to the useful product (MDB) are not obtained as they favour the formation of high quantities of dimeric by-products. The recovery of the catalyst from the reaction mixture, moreover, is not complete with the traditional systems and therefore requires particular and difficult operating conditions.

The Applicant has now found a process for the preparation of benzodioxols which not only overcomes the above disadvantages but also allows high reaction yields to be obtained as in processes based on DMSO. It has been found, in fact, that if the reaction according to scheme (I) is carried out in a polar aprotic solvent belonging to the group of N-alkylpyrrolidones such as, for example, N-methylpyrrolidone (NMP), it is possible not only to overcome the disadvantages typical of DMSO but also to obtain reactions yields even higher than 95%.

The present invention therefore relates to a process for the preparation of aromatic compounds containing a heterocyclic system having general formula (II):

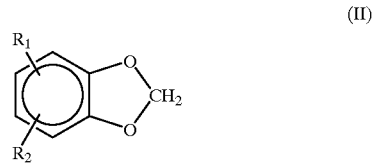

wherein $R_1$ and $R_2$, the same or different, represent a hydrogen atom, a halogen, a hydroxy, an alkyl halide radical or an alkoxy radical, containing from 1 to 6 carbon atoms (preferably from 1 to 4), a phenoxy radical, a $C_1$–$C_6$ alkyl radical (preferably $C_1$–$C_4$), a $C_2$–$C_6$ alkenyl radical (preferably $C_2$–$C_4$), a group selected from a —CHO formyl or carboxy radical, a —COCH$_3$ acetyl, —Y—CHO or —Y—COOH radical, wherein Y represents a $C_1$–$C_6$ alkylene radical (preferably $C_1$–$C_4$), or they represent an —NO$_2$ or —NR$_3$R$_4$ group, wherein $R_3$ and $R_4$, the same or different, are selected from a hydrogen atom or a $C_1$–$C_4$ alkyl radical, which comprises reacting catechol, optionally substituted, with a methylene dihalide in a basic environment and in the presence of a solvent medium consisting essentially of N-methylpyrrolidone.

According to the present invention preferred aromatic compounds containing a heterocyclic system are those in which the $R_1$ radical is a hydrogen atom whereas the $R_2$ radical represents a hydrogen atom, a methyl radical or a formyl radical respectively.

The synthesis reaction, which can be carried out by feeding the reagents either in continuous or batch, takes place between catechol, optionally substituted, and a methylene dihalide, for example methylene chloride, in the presence of a base to fix the halogen which develops during the reaction. Preferred bases according to the present invention are essentially carbonates and/or bicarbonates of alkaline metals such as sodium and potassium, or their mixtures. Potassium carbonate is particularly preferred, used with molar ratios catechol/$K_2CO_3$ ranging from 1/1 to 1/3, preferably between 1/1.2 and 1/1.5.

The reaction takes place at atmospheric pressure and at a temperature ranging from 50 to 170° C., preferably between 100 and 130° C.

Even if this synthesis adopts equimolar ratios between the reagents, it is preferable to carry out the process of the present invention with an excess of methylene dihalide to favour the almost total conversion of the catechol and to maintain an abundant reflux for the whole reaction, at the reaction temperature.

The NMP solvent is used in such quantities as to given a molar ratio catechol/solvent ranging from 1/2 to 1/20, preferably from 1/4 to 1/10.

At the end of the reaction, the benzodioxol thus prepared can be recovered by simple distillation. During this phase it is possible to recover the NMP solvent which is recycled to the synthesis.

Some illustrative but non-limiting examples are provided for a better understanding of the present invention and for its embodiment.

EXAMPLE 1

650 g of NMP (6.5 moles) and 173 g of $K_2CO_3$ (1.25 moles) are charged into a 1,000 cc reactor equipped with a stirrer, condenser and phase separator, thermometer and two distributors, one of which with a plunged pipe immersed in the reaction mixture. The suspension obtained is then heated to 130° C.

At this temperature, the feeding is initiated over a period of 4.5 hours of 110.11 g (1 mole) of catechol in the molten state.

The methylene chloride is fed in continuous contemporaneously, by means of the distributor with a plunged pipe immersed in the reaction mixture, and this feeding is continued for a further two hours after the feeding of the catechol has finished and in such a quantity as to maintain an abundant reflux at the reaction temperature.

The methylene chloride, after condensation and separation of the water, is recycled in the same reaction mixture.

The total reaction time at a temperature of 130° C. is about 6.5 hours.

The reaction mixture is cooled to room temperature for filtration and elimination of the filtered solid.

The solution, after filtration, is evaporated from the methylene chloride present and then distilled at reduced pressure in a rectifying column obtaining a pure fraction of MDB of 116.62 g (boiling point: 110° C. at 100 torr).

Catechol conversion: 100%.
Selectivity to MDB: 95.5%.

EXAMPLE 2

The same procedure is carried out as in example 1, charging 1.5 moles of $K_2CO_3$ (207 g). After filtration of the salts and distillation of the MDB, 115.4 g of pure product are obtained.

Catechol conversion: 100%.
Selectivity to MDB: 94.5%.

EXAMPLE 3

The same procedure is carried out as in example 2, but operating at a temperature of 120° C. After distillation, 110 g of pure MDB are obtained.

Catechol conversion: 100%.
Selectivity to MDB: 90.1%.

EXAMPLE 4

The same procedure is carried out as in example 1, charging 1.1 moles of $K_2CO_3$ (152 g). After filtration of the salts and distillation of the MDB, 114.79 g of pure MDB are obtained.

Catechol conversion: 100%.
Selectivity to MDB: 94.0%.

EXAMPLE 5

The same procedure is carried out as in example 1, charging 4-methylcatechol instead of catechol. After distillation in a stream of vapour with water, 127.3 g of pure 3,4-methylenedioxytoluene are obtained.

Conversion of 4-methylcatechol: 100%.
Selectivity to methylenedioxytoluene: 93.5%.

EXAMPLE 6

The same procedure is carried out as in example 1, charging 3,4-dihydroxybenzaldehyde in a solution of NMP instead of catechol. At the end of the reaction after separation by distillation under vacuum (residue of 10 mmHg) 141.6 g of pure 3,4-methylenedioxybenzaldehyde are obtained.

Conversion of 3,4-dihydroxybenzaldehyde: 100%
Selectivity to 3,4-methylenedioxybenzaldehyde: 93.5%.

EXAMPLE 7 (COMPARATIVE)

The same procedure is carried out as in example 1 except that the NMP solvent is substituted with an equal quantity of sulfolane.

At the end of the reaction a 100% conversion is obtained but with a reduction in the selectivity to 80%.

EXAMPLE 8 (COMPARATIVE)

The same procedure is carried out as in example 1 except that the NMP solvent is substituted with an equal quantity of dimethylformamide and the temperature is reduced to 100° C.

At the end of the reaction a 100% conversion is obtained but with a reduction in the selectivity to 80%.

The text and examples of the present invention have been deliberately limited to N-methylpyrrolidone as this is the most convenient and available among N-alkylpyrrolidones. Other alkyl or cycloalkyl pyrrolidones are obviously included in the scope of the present invention.

We claim:
1. A process for the preparation of aromatic compounds containing a heterocyclic system having general formula (II):

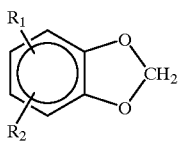
(II)

wherein $R_1$ and $R_2$, the same or different, represent a hydrogen atom, a halogen, a hydroxy, an alkyl halide radical or an alkoxy radical, containing from 1 to 6 carbon atoms, a phenoxy radical, a $C_1$–$C_6$ alkyl radical, a $C_2$–$C_6$ alkenyl radical, a group selected from a —CHO formyl or carboxy radical, a —COCH$_3$ acetyl, —Y—CHO or —Y—COOH radical, wherein Y represents a $C_1$–$C_6$ alkylene radical, or they represent an —NO$_2$ or —NR$_3$R$_4$ group, wherein $R_3$ and $R_4$, the same or different, are selected from a hydrogen atom or a $C_1$–$C_4$ alkyl radical, which comprises reacting catechol, optionally substituted, with a methylene dihalide in a basic environment and in the presence of a solvent medium consisting essentially of N-methylpyrrolidone.

2. The process according to claim 1, wherein the aromatic compounds containing a heterocyclic system are those in which the $R_1$ radical is a hydrogen atom and the $R_2$ radical represents a hydrogen atom, a methyl group or a formyl radical.

3. The process according to claim 1 or 2, wherein the synthesis reaction is carried out by feeding the reagents either in continuous or batch.

4. The process according to any of the previous claims, wherein the synthesis reaction takes place between catechol, optionally substituted, and methylene chloride, in the presence of an alkaline product selected from carbonates and/or bicarbonates of alkaline metals such as sodium and potassium, or their mixtures.

5. The process according to claim 4, wherein the alkaline product is potassium carbonate.

6. The process according to any of the previous claims, wherein the molar ratios catechol/K$_2$CO$_3$ are between 1/1 and 1/3.

7. The process according to any of the previous claims, wherein the synthesis reaction takes place at atmospheric pressure and at a temperature ranging from 50 to 170° C.

8. The process according to any of the previous claims, wherein the ratio catechol/N-methylpyrrolidone is between 1/1 and 1/20.

* * * * *